United States Patent [19]

Bethge et al.

[11] Patent Number: 5,621,117

[45] Date of Patent: Apr. 15, 1997

[54] METHOD FOR THE RACEMIZATION OF ENANTIOMERS OF α-LIPOIC ACID

[75] Inventors: Horst Bethge, Hanau; Roland Moeller, Hammersbach; Gerhard Sator, Dieburg; Stefan Merget, Rodgau; Thomas Beisswenger, Radebeul, all of Germany

[73] Assignee: ASTA Medica Aktiengesellschaft, Dresden, Germany

[21] Appl. No.: 504,557

[22] Filed: Jul. 20, 1995

[30] Foreign Application Priority Data

Jul. 30, 1994 [DE] Germany .......................... 44 27 079.8

[51] Int. Cl.$^6$ .................................................. C07D 339/04
[52] U.S. Cl. .................................................. 549/39
[58] Field of Search .................................................. 549/39

[56] References Cited

U.S. PATENT DOCUMENTS 4,772,727  9/1988  Sutherland et al. ...................... 549/39
5,281,722  1/1994  Blaschke et al. ........................ 549/39

FOREIGN PATENT DOCUMENTS 2029596  5/1991  Canada .
0694542  1/1996  European Pat. Off. .

OTHER PUBLICATIONS

Merck Index Abstract, p. 9165, 10th Edition (1983).

Primary Examiner—Jose' G. Dees
Assistant Examiner—Mary C. Cebulak
Attorney, Agent, or Firm—Beveridge. DeGrandi, Weilacher & Young, L.L.P.

[57] ABSTRACT

Method for the conversion of the enantiomers of α-lipoic acid into the corresponding racemic mixture by racemizing the α-lipoic acid (pure optical isomers of α-lipoic acid or mixtures of optical isomers of α-lipoic acid wherein one of the optical isomers is present in excess) at temperatures of between 110° C. and 200° C. at pressures of from normal pressure up to 50 bar for a reaction time of 10 to 48 hours.

16 Claims, No Drawings

METHOD FOR THE RACEMIZATION OF ENANTIOMERS OF α-LIPOIC ACID

INTRODUCTION AND BACKGROUND

The present invention relates to a method for converting the enantiomers of α-lipoic acid into the racemic mixture of α-lipoic acid.

α-lipoic acid is also referred to in the literature as 1,2-dithiolane-3-pentanoic acid or thioctic acid. α-lipoic acid is widely distributed in plants and animals as a coenzyme of α-keto acid dehydrogenases; the naturally-occurring form has the D-configuration and can be represented by the structural formula

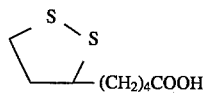

α-lipoic acid is pharmacologically active and possesses, among other features, antiphlogistic and antinociceptive (analgesic) as well as cytoprotective properties. An important medical indication is the treatment of diabetic polyneuropathy. In the case of the pure optical isomers of α-lipoic acid (D and L forms, that is, D-α-lipoic acid and L-α-lipoic acid), in contrast to the racemic mixture, the D-enantiomer is mainly antiphlogistic and the L-enantiomer is mainly antinociceptive (EP 0 427 247; CA 2,029,596); see also The Merck Index, 10th Edition, page 9165.

Known syntheses of the pure optical isomers of α-lipoic acid proceed, for example, via chiral precursors which are split in the course of the synthesis. Furthermore, the racemic α-lipoic acid can also be separated by conversion into salts of pure optical isomers of α-methylbenzylamine and crystallization, with the pure diastereomeric pair of salts first being isolated (U.S. Pat. No. 5,281,722 which is incorporated by reference in its entirety; DE 41 37 773.7). The disadvantage of the method cited is, however, that in each case the unwanted enantiomer as such can sometimes no longer be used therapeutically and the process of splitting to obtain the desired pure optical isomer of α-lipoic acid consequently becomes uneconomic.

The multiple stage method for preparing enantiomerically pure D(+) α-lipoic acid and L(−) α-lipoic acid avoids the splitting process but also proves to be inconvenient for commercial use (U.S. Pat. No. 4,772,727 which is incorporated by reference in its entirety; EP 0 261 336).

SUMMARY OF THE INVENTION

One object of the present invention is the conversion of pure optical isomers of α-lipoic acid, or mixtures of optical isomers of α-lipoic acid with one of the isomers being present in excess, into the racemic mixture of α-lipoic acid in order that the enantiomer which is inevitably formed in the classical splitting of racemic mixtures can be reused economically.

In one embodiment, the method for the racemization of pure optical isomers of α-lipoic acid or mixtures of optical isomers of α-lipoic acid wherein one of the optical isomers is present in excess involves racemizing the α-lipoic acid at temperatures of between 110° C. and 200° C. at pressures of from normal pressure up to 50 bar for a reaction time of 10 to 48 hours.

DETAILED DESCRIPTION OF THE INVENTION

Racemization of a compound is associated with the breaking and the renewal of atomic bonds, which in the case of α-lipoic acid appears to be difficult. α-lipoic acid contains a chemically and thermally sensitive —S—S— bridge and the centre of asymmetry is far removed from the functional —COOH group, so that steric interactions are decreased. Rearrangements and decomposition processes must therefore be expected during a racemization of α-lipoic acid, both under neutral conditions and in a base-catalyzed or an acid-catalyzed reaction.

α-lipoic acid (melting point 61° C.) and its pure optical isomers polymerize rapidly on heating with the formation of a sticky, tough polymeric α-lipoic acid which can no longer be further processed. Moreover, the polymeric thioctic acid melts on further heating and undergoes decomposition with a darkening in color. According to the present invention, however, it is now possible to establish conditions under which on the one hand the polymerization is avoided and on the other hand no decomposition takes place, but which surprisingly give rise to the racemization of the optical isomers. The optical isomer present in excess is racemized in the course of this method and at the end the α-lipoic acid used is present as a racemic mixture.

In achieving the above and other objects, one feature of the present invention resides in a process comprising suspending or dissolving in a suitable solvent as described below the unwanted pure optical isomer of α-lipoic acid, or the mixture of optical isomers of α-lipoic acid wherein one of the isomers is present in excess, and racemizing by treatment at temperatures of between 110° C. and 200° C. at a pressure of from normal pressure up to 50 bar for from 10 to 48 hours, with or without addition of auxiliary substances.

The racemization is carried out preferably in an organic solvent at a temperature of between 150° C. and 190° C. at a pressure of from normal pressure up to 20 bar for 10 to 48 hours, with optionally a further quantity of from 0.01 mol % to 5 mol % of acidic or basic auxiliary substances being added. The racemization is particularly preferably carried out in organic solvents with or without the addition of water at temperatures of between 150° C. and 180° C. at a pressure of up to 10 bar for 20 to 26 hours. The pressure conditions are dependent on the temperature, with a higher pressure building up at a higher temperature.

Besides water, examples of suitable solvents are aliphatic hydrocarbons having a carbon chain length of between 3 and 10, aromatic hydrocarbons which are liquid, esters of aliphatic or cycloaliphatic carboxylic acids having 2 to 6 carbon atoms, and aliphatic or cycloaliphatic alcohols having 2 to 6 carbon atoms, ethers and glycol ethers, or homogeneous mixtures of the said solvents. Particularly preferred solvents are, for example, toluene, xylene, o-dichlorobenzene, ethyl acetate and cyclohexane.

Suitable auxiliary substances are acidic or basic additives to the pure α-lipoic acid, the suspension or solution thereof. Besides inorganic mineral acids and Lewis acids, suitable acids are aromatic sulphonic acids and carboxylic acids having a chain length of 1 to 3. Besides inorganic bases, aliphatic and aromatic amines and amino compounds are suitable. Examples of such auxiliary substances which may be used are acetic acid, p-toluenesulphonic acid, ethyl acetate, triethylamine (TEA), morpholine, and other similar compounds.

The racemized α-lipoic acid can be obtained directly or by filtration from a suspension. The racemization solutions are also suitable for crystallizing pure optical diastereomeric pairs of salts directly according to the method cited above (DE 41 37 773.7; U.S. Pat. No. 5,281,722).

The racemic mixture of α-lipoic acid formed can then be split again by the method referred to in DE 41 37 773.7 (U.S. Pat. No. 5,281,722) and supplies more of the desired pure optical enantiomer. The selective preparation of a desired pure optical isomer of α-lipoic acid thereby becomes far more economic and also more advantageous from an ecological aspect. Since according to the present findings the D (+) enantiomer exhibits more pharmacologically significant effects, the L (–) enantiomer or mixtures of optical isomers containing an excess (e.g., more than 50%) of the L (–) enantiomer were mainly used in the racemization. The D (+) enantiomer or mixtures of optical isomers containing an excess (e.g., more than 50%) of the D (+) enantiomer can obviously be racemized in an identical manner. The yields during the racemization, depending on the reaction conditions, are approximately 70% with a racemized proportion of an enantiomer of up to 49%.

The purity of the optical isomers was determined from the specific optical angles of rotation. In addition, relative contents of the optical isomers of α-lipoic acid were determined with a detection limit of greater than 0.5% by means of HPLC on optically active columns. A homogeneous sample of the respective reaction material was used for this purpose. Such procedures and equipment are well known in the art.

In another embodiment of the present invention, the method for the racemization of pure L-(–)-α-lipoic acid involves racemizing a pure L-(–)-α-lipoic acid in at least one inert organic solvent at temperatures of between 110° C. and 200° C. at pressures of from normal pressure up to 50 bar for a reaction time of 10 to 48 hours, distilling off the inert organic solvent while maintaining a temperature between 40° to 50° C. to produce an oily residue, adding at least two inert organic solvents to the oily residue and heating at 40° to 50° C. until a clear yellow solution is obtained, adding a cellulose filtration accelerator to the clear yellow solution and stirring for approximately 5 minutes, filtering and washing with the same at least two inert organic solvents, cooling to at least about 5° C. for the α-lipoic acid to crystallize out, further cooling to about –5° C. followed by stirring at about –5° C. for about 2 hours, filtering and rewashing using at least one inert organic solvent, and drying under vacuum at 20 to 25° C.

The present invention is explained in more detail by means of the following Examples (unless other indicated pure L-(–)-α-lipoic acid or D-(+)-α-lipoic acid was used in the examples):

EXAMPLE 1

75 g of L-(–)-α-lipoic acid was stirred at 150° C. under nitrogen. After 22 h the acid was cooled. The content of D-(+)-α-lipoic acid was 3%.

EXAMPLE 2

75 g of L-(–)-α-lipoic acid was stirred at 160° C. under nitrogen. After 22 h the acid was cooled. The content of D-(+)-α-lipoic acid was 15.3%.

EXAMPLE 3

75 g of L-(–)-α-lipoic acid was stirred at 170° C. under nitrogen. After 22 h the acid was cooled. The content of D-(+)-α-lipoic acid was 47.8%.

The yields of the racemizations in solid form decrease, however, owing to the rates of decomposition of α-lipoic acid from 160° C. upwards.

EXAMPLE 4

75 g of D-(+)-α-lipoic acid was stirred at 170° C. under nitrogen. After 22 h the acid was cooled. The content of L-(–)-α-lipoic acid was 48.1%.

EXAMPLE 5

50 g of D-(+)-α-lipoic acid and 25 g of L-(–)-α-lipoic acid was stirred at 170° C. under nitrogen. After 22 h the solution was cooled. The content of L-(–)-α-lipoic acid was 49.5%.

EXAMPLE 6

50 g of L-(–)-α-lipoic acid and 50 g of D-(+)-α-lipoic acid was stirred at 170° C. under nitrogen. After 22 h the solution was cooled. The content of L-(–)-α-lipoic acid was 49.5%.

EXAMPLE 7

Variants:

Solvent: toluene

Temperature: 180° C.

Inherent pressure: 6 bar 75 g of L-(–)-α-lipoic acid was dissolved in 300 ml toluene (clear yellow solution). This solution is placed in a 1000 ml autoclave. The autoclave is closed and the solution is then heated to 180° C. and stirred for 24 hours at this temperature. An inherent pressure of approx. 6 bar is established.

At the end of the contact time the solution is removed from the autoclave and the toluene is distilled off under vacuum, while the temperature of the bottom of the column is between 40° to 50° C.

500 ml of a mixture consisting of 333 ml of cyclohexane and 167 ml of ethyl acetate is added to the oily residue left behind in the bottom of the column and the mixture is heated to 40° to 50° C. After a short time a clear yellow solution is obtained.

1 g of Diacel® cellulose filtration accelerator from the firm Cellulose-Füllstoff-Vertriebs GmbH (Mönchengladbach, Germany) is added to the solution, which is then stirred for 5 minutes.

The mixture is then filtered under suction using a nutsch filter and washed with 50 ml of a mixture of cyclohexane and ethyl acetate. The filtrate is cooled slowly with stirring. Crystallization of the α-lipoic acid begins at about 5° C. After the α-lipoic acid has crystallized out, cooling is continued to about –5° C. followed by stirring at this temperature for 2 hours. The product is then filtered under suction using a nutsch filter and rewashed with 50 ml of cyclohexane. The α-lipoic acid, which is moist from the solvent, is dried under vacuum (10 to 20 mm bar) at 20° to 25° C.

57 g of α-lipoic acid $\alpha_D^{20}=0°$ (c=1, ethanol) is obtained. This corresponds to a yield of 76%.

The proportion of D(+)α-lipoic acid is 49%.

The α-lipoic acid remaining in the mother liquor can be partly recycled by crystallization from the mother liquor after the latter has been evaporated to one third of its volume. This second crystallizate has to be recrystallized.

The starting material used in examples 8–15 was L-(–)-α-lipoic acid:

Further racemizations were carried out under the following conditions:

| Example No. | Temperature [%] | Solvent | Duration of reaction [h] | Pressure [bar] | D-(+)-α-LA portion [%] | Yield dry [%] |
|---|---|---|---|---|---|---|
| 8 | 150 | Toluene | 24 | 4.2 | 21.9 | 76.3 |
| 9 | 150 | Toluene (3% TEA) | 24 | 4 | 10.4 | 50.8 |
| 10 | 150 | Toluene (3% acetic acid) | 24 | 3.5 | 25.9 | 44.1 |
| 11 | 150 | Toluene (3% water) | 24 | 6 | 27.8 | 74.5 |
| 12 | 150 | Xylene | 24 | 1.9 | 16.9 | 58.9 |
| 13 | 150 | Cyclohexane/ethyl acetate (1:1) | 24 | 7.5 | 17.8 | 48.5 |
| 14 | 176 | n-decane | 24 | Normal pressure | 37.7 | 73.1 |
| 15 | 184 | o-dichloro-benzene | 24 | Normal pressure | 49.2 | 73.6 |

LA = lipoic acid

The relative contents of the optical isomers of α-lipoic acid were determined by means of HPLC on optically active columns.

Separation of enantiomers of DL-thioctic acid on chiral supporting material:

Chromatographic Conditions

Column: Chiral AGP (Firm ICT)

Column dimensions: 100 mm×4 mm

Guard column: Chiral AGP (Firm ICT)

Column dimensions: 100 mm×3 mm

Mobile phase: 1000 ml 0.01m disodium hydrogen phosphate solution adjusted to a pH value of 4.95 to 5.05 with dilute phosphoric acid, 150 ml of methanol added and thoroughly mixed.

Flow rate: 0.5 ml/min

Pressure: approx. 35 bar

Temperature: 20° C.

Wavelength: 210 nm

Preparation of Sample

About 1.5 to 2 mg of the respective enantiomers are dissolved in 1 ml of methanol and diluted to 20 ml with the mobile phase. The solution is filtered through a 0.45 μm membrane filter as required. 20 μl of this solution is injected.

Further variations and modifications of the foregoing will be apparent to those skilled in the art and such variations and modifications are intended to be encompassed by the claims that are appended hereto.

German Priority Application P 44 27 079.8, filed on 30 Jul. 1994, is relied on and incorporated by reference in their entirety.

We claim:

1. A method for the racemization of pure optical isomers of α-lipoic acid or mixtures of optical isomers of α-lipoic acid wherein one of the optical isomers is present in excess, said method comprising racemizing the α-lipoic acid at temperatures of between 110° C. and 200° C. at pressures of from normal pressure up to 50 bar for a reaction time of 10 to 48 hours.

2. The method according to claim 1, wherein said temperature is between 150° C. and 190° C. and wherein said pressure is from normal pressure up to 20 bar.

3. The method according to claim 1, wherein said temperature is between 150° C. and 180° C., wherein said pressure is from normal pressure up to 10 bar, and wherein said time is for 20 to 26 hours.

4. The method according to claim 1, wherein acidic or basic auxiliary substances are added in a proportion of from 0.01 mol % to 5 mol %.

5. The method according to claim 4, wherein said acidic auxiliary substances are selected from the group consisting of inorganic mineral acids, Lewis acids, aromatic sulphonic acids, carboxylic acids having a chain length of 1 to 3, and mixtures thereof, and wherein said basic auxiliary substances are selected from the group consisting of inorganic bases, aliphatic amines, aromatic amines, amino compounds and mixtures thereof.

6. The method according to claim 5, wherein said acidic auxiliary substances are selected from the group consisting of acetic acid, p-toluenesulphonic acid, and ethyl acetate, and wherein said basic auxiliary substances are selected from the group consisting of triethylamine and morpholine.

7. The method according to claim 1, wherein said time is from 20 to 40 hours.

8. The method according to claim 1, wherein said lipoic acid is the L (−) enantiomer or mixtures of optical isomers containing an excess of the L (−) enantiomer.

9. The method according to claim 1, wherein said α-lipoic acid is in solid form, in suspension, or in a mixture of at least one inert solvent.

10. The method according to claim 1, wherein said α-lipoic acid is in liquid form.

11. The method according to claim 1, wherein said method further comprises adding water.

12. The method according to claim 1, wherein said method further comprises recovering the desired isomer of α-lipoic acid.

13. The method according to claim 1, wherein said method consisting essentially of racemizing the α-lipoic acid at temperatures of between 110° C. and 200° C. at pressures of from normal pressure up to 50 bar for a reaction time of 10 to 48 hours.

14. A method for the racemization of pure L-(−)-α-lipoic acid, said method comprising racemizing the pure L-(−)-α- lipoic acid in at least one inert organic solvent at temperatures of between 110° C. and 200° C. at pressures of from normal pressure up to 50 bar for a reaction time of 10 to 48 hours, distilling off said inert organic solvent while maintaining a temperature between 40° to 50° C. to produce an oily residue, adding at least two inert organic solvents to said oily residue and heating at 40° to 50° C. until a clear yellow solution is obtained, adding a cellulose filtration accelerator to said clear yellow solution and stirring for approximately 5 minutes, filtering and washing with said at least two inert organic solvents, cooling to at least about 5° C. for the α-lipoic acid to crystallize out, further cooling to about −5° C. followed by stirring at about −5° C. for about 2 hours, filtering and rewashing using at least one inert organic solvent, and drying under vacuum at 20° to 25° C.

15. The method according to claim 9, wherein said solvent is selected from the group consisting of water, aliphatic hydrocarbons having a carbon chain length of between 3 and 10, aromatic hydrocarbons which are liquid, esters of aliphatic carboxylic acids having 2 to 6 carbon atoms, cycloaliphatic carboxylic acids having 2 to 6 carbon atoms, aliphatic alcohols having 2 to 6 carbon atoms, cycloaliphatic alcohols having 2 to 6 carbon atoms, ethers, glycol ethers, and homogeneous mixtures thereof.

16. The method according to claim 15, wherein said solvent is selected from the group consisting of toluene, xylene, o-dichlorobenzene, ethyl acetate, cyclohexane, n-decane and mixtures thereof.

* * * * *